United States Patent
Mueller

(10) Patent No.: US 8,777,886 B2
(45) Date of Patent: Jul. 15, 2014

(54) COMPRESSION BANDAGE AND METHOD FOR ITS MANUFACTURE

(75) Inventor: Markus Mueller, Albstadt (DE)

(73) Assignee: Peter Mueller GmbH, Albstadt (DE)

( * ) Notice: Subject to any disclaimer, the term of this patent is extended or adjusted under 35 U.S.C. 154(b) by 186 days.

(21) Appl. No.: 12/932,987

(22) Filed: Mar. 10, 2011

(65) Prior Publication Data

US 2011/0224594 A1  Sep. 15, 2011

(30) Foreign Application Priority Data

Mar. 11, 2010  (DE) .......................... 10 2010 011 840

(51) Int. Cl.
*A61L 15/00* (2006.01)

(52) U.S. Cl.
USPC .................... 602/75; 66/61; 602/61

(58) Field of Classification Search
USPC ............................. 602/75–76, 60–65; 66/61
See application file for complete search history.

(56) References Cited

U.S. PATENT DOCUMENTS

| | | | |
|---|---|---|---|
| 2,280,025 A | | 4/1942 | Bollinger |
| 4,911,156 A | * | 3/1990 | Libertucci ........................ 602/62 |
| 5,439,438 A | * | 8/1995 | Ersfeld et al. ..................... 602/3 |
| 6,425,876 B1 | * | 7/2002 | Frangi et al. .................... 602/60 |

FOREIGN PATENT DOCUMENTS

| | | |
|---|---|---|
| CH | 103772 A | 3/1924 |
| DE | 860 531 C | 12/1952 |
| DE | 87 02 573 U1 | 7/1987 |

OTHER PUBLICATIONS

Search report issued in European Application No. 11155223.8 dated Aug. 11, 2011 with English translation of category of cited documents (5 pages).

\* cited by examiner

*Primary Examiner* — Patricia Bianco
*Assistant Examiner* — Camtu Nguyen
(74) *Attorney, Agent, or Firm* — Flynn, Thiel, Boutell & Tanis, P.C.

(57) ABSTRACT

A compression bandage with a tubular, flexible flat material for surrounding a bodily member and with a number of elastic compression threads, whereby this flat material constitutes a main body that can be stretched in the circumferential direction. A number of elastic compression threads run in the plane of the flat material in the direction of the circumference, and create the compressive effect when the compression bandage is applied. At least parts of at least some of the compression threads protrude outside the flat material, allowing the compressive effect to be adjusted by varying the length of each of the protruding external portions.

13 Claims, 3 Drawing Sheets

COMPRESSION BANDAGE AND METHOD FOR ITS MANUFACTURE

FIELD OF APPLICATION AND PRIOR ART

This application claims the priority of the German patent application No. 10 2010 011 840.0. The whole disclosure of this prior application is herewith incorporated by reference into this application.

The invention relates to a compression bandage for surrounding a bodily member with a tubular, flexible flat material for surrounding the bodily member and having a number of elastic compression threads. The flat material constitutes a main body of the compression bandage that can be stretched in the circumferential direction. The compression threads extend in the plane of the flat material, passing through the flat material in the circumferential direction; when the compression bandage is applied, they generate the intended compression effect. The invention also relates to a method for manufacturing a compression bandage.

Compression bandages of this type are familiar to the prior art. They are used to compress a patient's bodily member, in particular an arm or leg, for therapeutic purposes. Compression bandages of this type are particularly used in the context of therapy for oedemas such as lymphatic oedemas.

The tubular flat material that constitutes the main body of the compression bandage is pulled over the bodily member under treatment, as a result of which the elastic compression threads that are contained in the main body and which, when applied, extend round the bodily part, are stretched as the bandage is applied, so generating the desired compression effect. Compression bandages of this type are available in a variety of compression classes; typically, classes I to IV are distinguished, differing in the degree of compression that they generate.

Even when, in the context of a therapeutic application, a compression bandage of this type is used that is intended to apply a constant compressive pressure throughout the duration of the therapy, this has formerly nevertheless led to the need to use different compression bandages at different stages of the therapy, since the desired therapeutic effect, in particular in the presence of oedemas, can have the result that the bodily part under treatment reduces in circumference. Retaining the same compression bandage would therefore lead to a continuously reducing degree of compression.

This problem is usually dealt with by applying new compression bandages to the patient as the therapy proceeds; these bandages must, at some expense, be made individually. Reworking existing compression bandages is not usually possible here, as the cuts that would be necessary in bandages that no longer fit would have the effect that the compression threads would lose their grip, and would no longer be able to generate their effect. In particular, opening, for example, the tubular main body followed by cutting off a region at the edge of the flat material of the main body in order to reduce the circumference is out of the question, since, as indicated above, the compression threads that were attached in the edge region that was cut would no longer be held at both ends, and could therefore no longer generate their effect.

A compression bandage of an open form is known to the prior art. In such cases, the tubular form is created by joining edges of the bandage area which, before use, are separate and at opposite sides, using a Velcro fastener to match the specific requirements. A particular, desired compressive effect can, however, only be created in this way very approximately. A Velcro fastener of this type is, moreover, very easily manipulated by patients, and this creates a risk that the patient, by changing the circumference of the compression bandage, will change the previously set configuration and therefore the desired compressive effect.

The task of the invention is to provide a compression bandage of this general type that avoids the disadvantages of the prior art. This is achieved according to this invention in that, in a compression bandage of this general type, at least some sections of at least some of the compression threads protrude out of the flat material, allowing the compressive effect to be adjusted by varying the length of each of the protruding external segments.

A compression bandage according to the invention thus has the tubular main body described above, through which the compression threads run. This tubular main body has a closed form and will not, when used according to its proper purpose, be opened in its circumference either by the medical staff who are applying the bandage or by the patient. In order to adapt the compressive effect individually, at least some of the compression threads that run around the circumference are brought to the outside, out of the main body, so that by changing a fraction of the compression thread that constitutes the external portion, the compressive effect of the compression thread can be specifically adjusted. In particular, a compression bandage that has already been applied in the context of a therapy can be readjusted so that a consistent compressive effect can be achieved even after some of the desired reduction in the circumference of the body part has occurred in the course of the therapy.

The compression threads surround at least the majority of the body part. By using a circular knitted fabric as the main body, it is also possible to fully surround the body part. Nevertheless, surrounding at least 75% of the body part, i.e. a wrapping angle of 270°, is considered preferable. The compression bandage according to the invention incorporates a large number of compression threads that are aligned around the circumference and which are to a large extent parallel to one another. In the sense of this invention, sections of a common thread that are aligned parallel to one another and which are formed, for instance, as weft threads with orientations that change by 180° and offset from one another as they pass through the main body, are looked on as separate compression threads. If a textile flat material is used for the main body it is possible, in particular, for the compression threads to be passed through its stitches, so that separate guiding channels do not have to be provided for them.

The compression threads consist favourably of rubber, in particular of natural rubber. It is also possible to use a synthetic material such as elastane. In order to achieve a desired frictional relationship with the yarn that has been formed into the main body it may be appropriate for the compression threads to have a layer of conventional yarn surrounding a core of rubber or elastane. Depending on the specific compression bandage, it may be advantageous either to achieve a very low coefficient of friction or to achieve a high coefficient of friction. Low friction makes relative movement between the compression threads and the main body occur more easily, so that a substantially homogeneous degree of compression is arrived at around the circumference of the compression bandage. A high friction, on the other hand supports fixing a compressive effect achieved by varying the length of the external portion.

The protruding external portions of the compression threads must be fixed by a means of fastening in such a way that the configuration that has been set up by a skilled person is retained.

The main body, which consists of the flexible flat material, is favourably implemented as a textile main body. As has been explained above, it can be implemented as a circular knitted fabric. It is nevertheless considered advantageous for the flat material to be fabricated by joining the opposite edges of an item of flat material. In such a case use is made of a flat material, in particular flat knitted material, in which the opposing edges are joined by a seam or similar technique, in order to thus form the tubular main body. This method of manufacture in particular makes it easily possible to create a main body whose shape varies from the cylindrical by varying the number of stitches in each row of stitches, as may, for instance, be necessary for a leg bandage or a support stocking.

When a flat material, in particular a flat woven material, of this sort is used it is particularly advantageous if the compression threads consist, at least in part, of a common thread that passes back and forth a number of times between the opposite edges of the flat material. This simplifies manufacture, as the elastic compression threads can be incorporated as weft threads during the manufacture of the flat material.

It is of particular advantage here if exit locations, where the external portions of the compression threads emerge from the flat material, are at some distance from the associated edge, advantageously by at least five millimeters, and in particular by at least 10 millimeters. The compression threads, which in the case of a woven flat material extend between two edges that are to be sewn together, can be kept away from the area of the seam between the edges through positioning these exit locations at a distance from the edge, so that the seam does not impair movability at the exit locations. It is particularly advantageous if those parts of the flat material that are beyond these exit locations, and which are therefore free of compression threads, are reinforced and/or stiffened in comparison with the rest of the main body, so that creases do not develop here even though there are no compression threads in this region.

For the sake of being able to adjust the various lengths of the external portions of the compression threads conveniently it is preferable for a number of the compression threads protruding from the flat material to be joined by a common handling section, by means of which these compression threads can partially be pulled out of the flat material. This handling section thus makes it possible for several or all compression threads to be adjusted at the same time.

It is also possible to provide a number of handling sections each of which is joined to a number of compression threads, so that by means of the different handling sections in different partial areas of the compression bandage, a degree of compression desired for individual parts of the body can be set specifically.

The handling section or sections can consist of substantially rigid components, for instance of single-piece plastic segments.

It is, however, of particular advantage if the handling section or sections is or are flexible, so that the compression threads that are bonded at different locations to this variable-shape handling section can be pulled out of the main body to different degrees, in order to permit adjustment of the compressive effect for specific areas.

It is particularly advantageous here for the handling section to comprise a textile section that is only connected to the flat material by the compression threads, whereby its stitches can guide and support the compression threads.

The implementation with a textile handling section offers, in addition to tactile advantages, an additional significant advantage to manufacture of the compression bandage, since the main body, or the flat knitted material constituting the main body, and the handling section, or its flat knitted material, can be manufactured in a common processing stage. This will be explained further below.

As has been explained above, a means of fastening is required in order to fix a condition that has previously been achieved by pulling the compression threads from the main body to the degree appropriate for therapy. It is advantageous for the handling section itself to be fastened or attached to the outside of the main body by this means of fastening. The means of attachment can, for instance, be implemented here as a Velcro fastener or by hooks that hook into the stitches of the main body. It is nevertheless advantageous if the means of fastening is formed in such a way that it cannot be released by the patient without the aid of a tool. This prevents the patient from intentionally or unintentionally changing the configuration that has been set up by skilled personnel. The means of fastening can, for instance, be implemented in such a way that it can only be released by means of a special tool, such as a rivet opener or a source of heat. Preferred examples of means of fastening that cannot be released by the patient without difficulty include a stitched seam and a riveted, welded or glued joint.

If a riveted joint is used, it is preferable for the main body and/or the handling section already to have recesses that can accept the rivets. If a stitched seam is used it is preferable to use a type of stitch which does not lose stability in the presence of local damage, for instance by knotting the thread of which the seam is formed. This prevents accidental damage of the seam leading immediately to loss of the compressive effect that has been set up.

A compression bandage according to the invention can favourably be formed as an arm bandage, as a leg bandage or as a compression stocking. In the case of an arm bandage, a compression bandage according to the invention favourably has a length of up to 30 cm. As a leg bandage, a compression bandage according to the invention favourably has a length of more than 40 cm. Compression stockings may have a length of up to 105 cm. They may be open or closed at the toe end.

It may be advantageous, in particular for leg bandages, for the compression threads to be arranged in such a way that zones of reduced tension are created, for instance in the region of the kneecap. These zones of reduced tension can be created by incorporating a rigid insert in the main body.

A compression bandage according to the invention can be manufactured by first fabricating the bandage in the usual way, after which the compression threads contained in the circular knitted fabric, or the flat knitted fabric whose edges have been joined, are pulled individually out of the fabric along a line that extends along the main length of the bandage in order that they may then be joined to, for instance, a common handling section.

Particularly advantageous, however, is a manufacturing procedure for the manufacture of a compression bandage according to the invention in which the flexible flat material is made as a flat knitted fabric on a knitting machine, whereby the compression threads are incorporated into the flat knitted fabric during the knitting process, and whereby an external portion of at least a part of the compression thread is drawn out of the flexible flat material during the knitting process. Two opposing edges of the flat knitted material are then joined together in order in this way to create the tubular main body.

The external portions brought out during the knitting process can then be used for the adjustment of the compression bandage described above. Their external length is favourably at least 10 millimeters. This facilitates the subsequent connection to a handling section. Favourably the location where the compression threads emerge is at a distance from the edges of the flat knitted material that are to be joined.

Of particular advantage is a variant of the manufacturing process in which the knitting machine, at the same time as and in parallel with the manufacture of the flexible flat material of the main body, fabricates a handling section, also comprised of flat knitted material, whereby the free ends of the external portions of the compression threads are inserted into the flat knitted material of the handling section and are attached in that way.

In this embodiment it is accordingly arranged that the knitting machine simultaneously makes both the rows of stitches in what will later be the main body and the rows of stitches in the handling section. The compression threads, favourably in the form of a continuous weft thread, are here passed from what will later be the main body to the handling section and, when appropriate, passed back again. The result of this method is the creation of two items of flat knitted fabric, representing what will later be the main body and the handling section; these are only joined together by the compression threads. The compression threads thus extend over a gap that remains between the two items of flat knitted material.

In addition to the fact that in this way a bandage according to the invention can be manufactured in just a few steps, this method has the advantage that the external portions of the compression threads that have been brought out are not likely to develop knots or become tangled in some other way even before the handling section has been attached.

BRIEF DESCRIPTION OF THE DRAWINGS

Further aspects and advantages of the invention will emerge from the following description of one favourable embodiment of the invention which is explained with the aid of the figures, in which.

DETAILED DESCRIPTION

The embodiment explained below concerns a compression bandage for a leg to be worn in the region of a patient's knee. This type of compression bandage is only to be understood as an example. The method of manufacture described below and the configuration of the compression bandage also apply equally to other kinds of compression bandages, in the form, for instance, of compression stockings or arm bandages.

Figure 1:
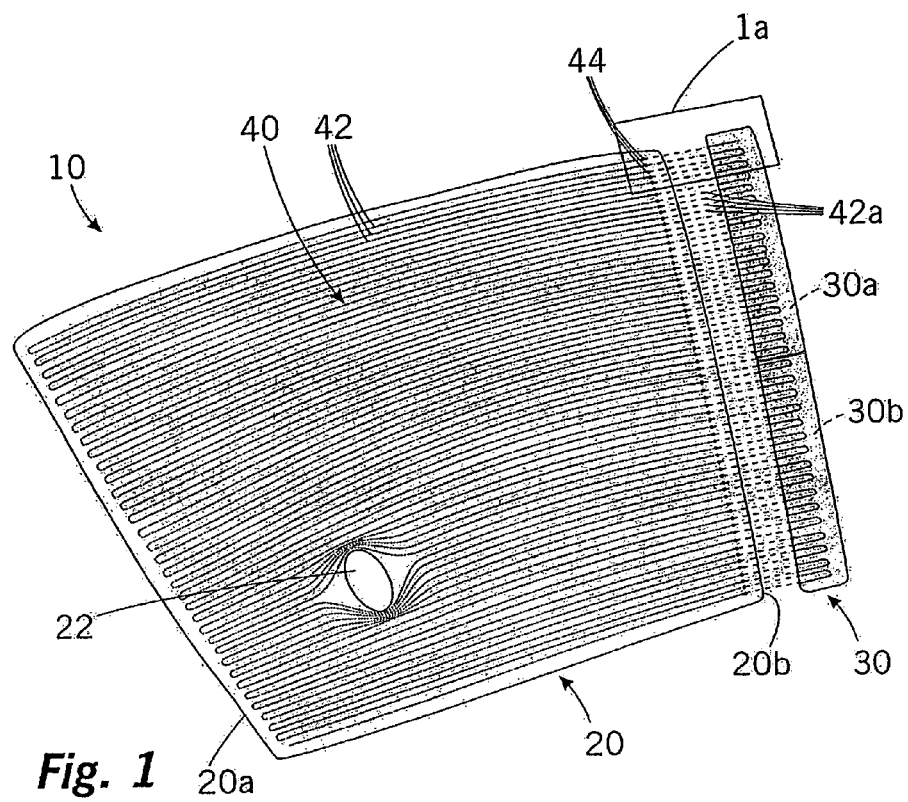
FIGS. 1 and 1a show a semi-finished product for the manufacture of a compression bandage according to the invention.

FIG. 1 illustrates the compression bandage according to the invention in a state where manufacture is not yet complete.

In this condition, what will later become the compression bandage 10 consists of a flat woven material 20 that will later become the main body 50 and a narrow strip of flat knitted material 30 that will later form the handling section 60. The items of flat knitted material 20, 30 naturally consist, as is illustrated in FIG. 1, of individual rows of stitches, whereby the yarn used may consist of the substantially inelastic polyamide 6.6. This may, if appropriate, be combined with an elastic thread of elastane.

An approximately elliptical plastic insert 22 is incorporated into the flat knitted material 20 to be located later in the area of the knee, its purpose being to keep the area which will later be on the knee largely free from tension.

During the manufacture itself of the flat knitted material 20, 30, a rubber thread 40 consisting of natural rubber is incorporated as a weft thread, whose substantially mutually parallel sections 42 are referred to, in the sense of this invention, as compression threads 42. These compression threads 42 extend from what is shown in FIG. 1 as the left hand edge 20a of the flat knitted material 20 across almost as far as its right hand edge 20b. About 10 mm before the right-hand edge 20b the compression threads 42 emerge from the flat knitted material 20 on its front side through exit locations 44. These exit locations 44 are each represented in the figures as circular openings. Favourably, however, they merely consist of gaps between rows of stitches, and they therefore do not have a circular form.

On the far side of the exit locations 44, the compression threads constitute external portions 42a that are taken to the strip of flat knitted fabric 30 that will later form the handling section 60. The external portions are held there by the stitches of the flat knitted fabric 30.

Figure 1A:
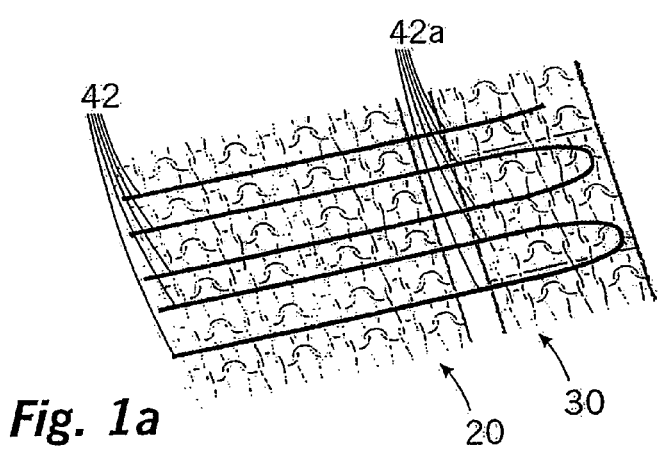

The manufacture of the two flat knitted fabric pieces 20, 30 of FIG. 1 is carried out on a knitting machine which creates the two flat knitted fabric pieces 20, 30 simultaneously, thereby creating the rows of stitches of the flat knitted fabric pieces 20, 30 that are illustrated in FIG. 1a before then forming the next row of stitches of the flat knitted fabric pieces 20, 30. The rubber thread 40 that constitutes the compression thread 42 is incorporated during the manufacture of the rows of stitches as a weft thread. Separate inclusion of the compression threads 42 is therefore not needed. Instead, they are introduced into the stitches and attached during manufacture of the flat knitted fabrics 20, 30 in the manner that is illustrated, in particular in FIG. 1a.

In order to complete manufacture of the finished compression bandage 10 starting from the condition shown in FIG. 1 it is only still necessary to join the opposite edges 20a, 20b of the flat knitted fabric 20. The flat knitted fabric 20 is brought in this way into a tubular form that constitutes the main body 50 of the compression bandage 10.

Figure 2A:
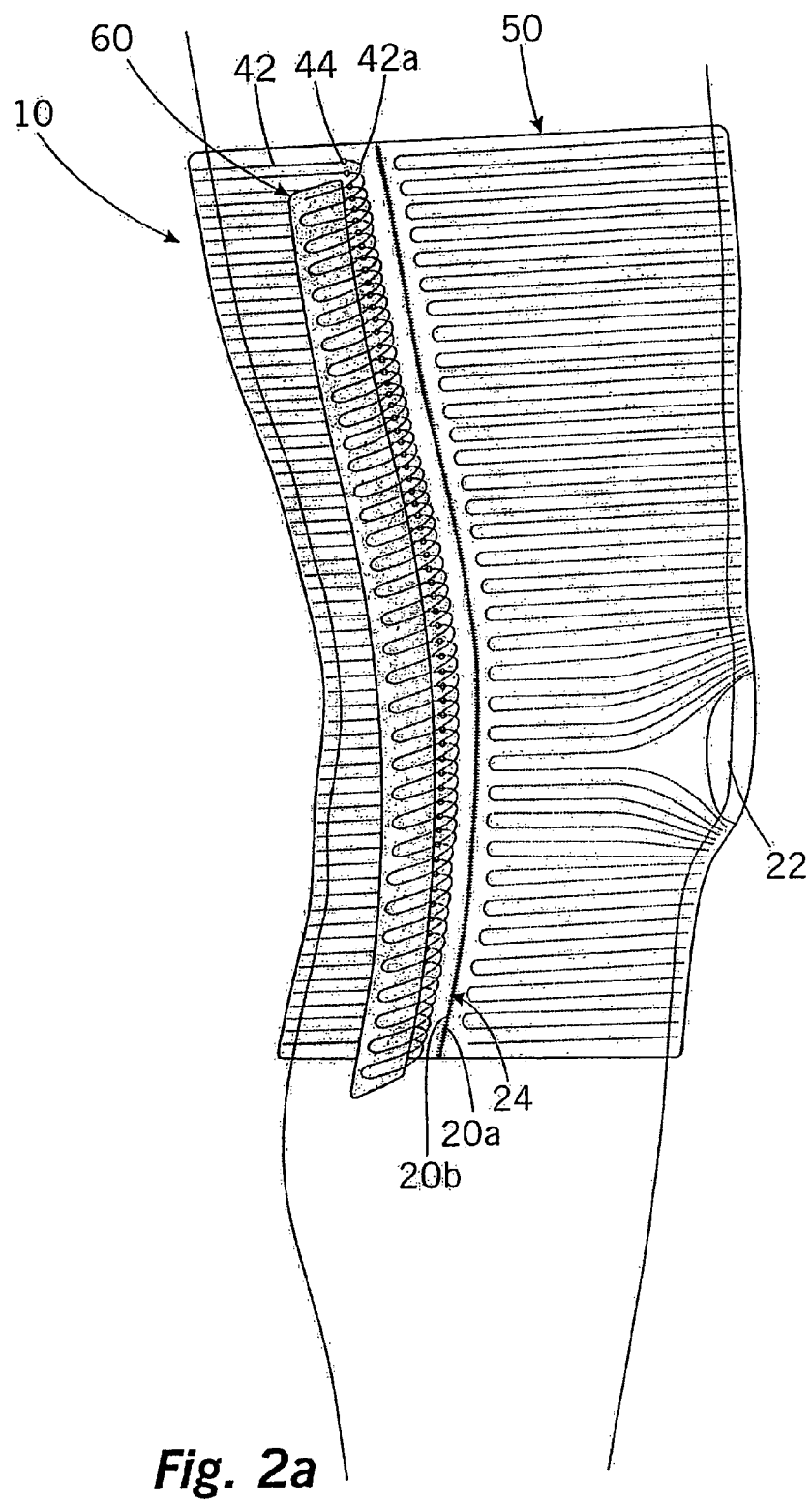
FIGS. 2a to 2c show the ability to adjust the compression bandage.

The finished compression bandage 10 is shown applied to a patient in FIG. 2a. It can be seen that the flat knitted fabric 20 is joined, in the region of its edges 20a, 20b by means of a seam 24, so constituting the tubular main section 50. The compression threads 42 extend from both sides, reaching close to the seam 24. From the point of view of the perspective shown in FIG. 2a, they are brought through the exit locations 44 described above to the left of the seam 24 and are then joined, as has already been described, to the handling section 60 that is constituted by the flat knitted material 30 illustrated in FIG. 1.

FIG. 2a illustrates the condition in which the compression bandage has already been applied but has not yet been adjusted to the individual therapeutic requirements of the patient. This is done, after initial application, in the manner illustrated in FIGS. 2a to 2c.

Depending on the compressive effect that is to be established, the handling sections 60 are used to pull the compression threads 42 out of the main body 50 to equal or to different degrees, so that the proportion of the compression threads 42 that remains in the main body 50 is modified. The larger the external portion 42a of each compression thread 42, the stronger the compressive effect.

In order to fix a condition that has been set up, the handling section 60 is fastened to the main body 50 using a means of fastening 70. This means of fastening can, for instance, be implemented by a Velcro fastener, not shown, one of whose complementary surfaces is located on the inside of the handling section 60, the other on the outside of the main section 50.

Figures 2B, 2C:
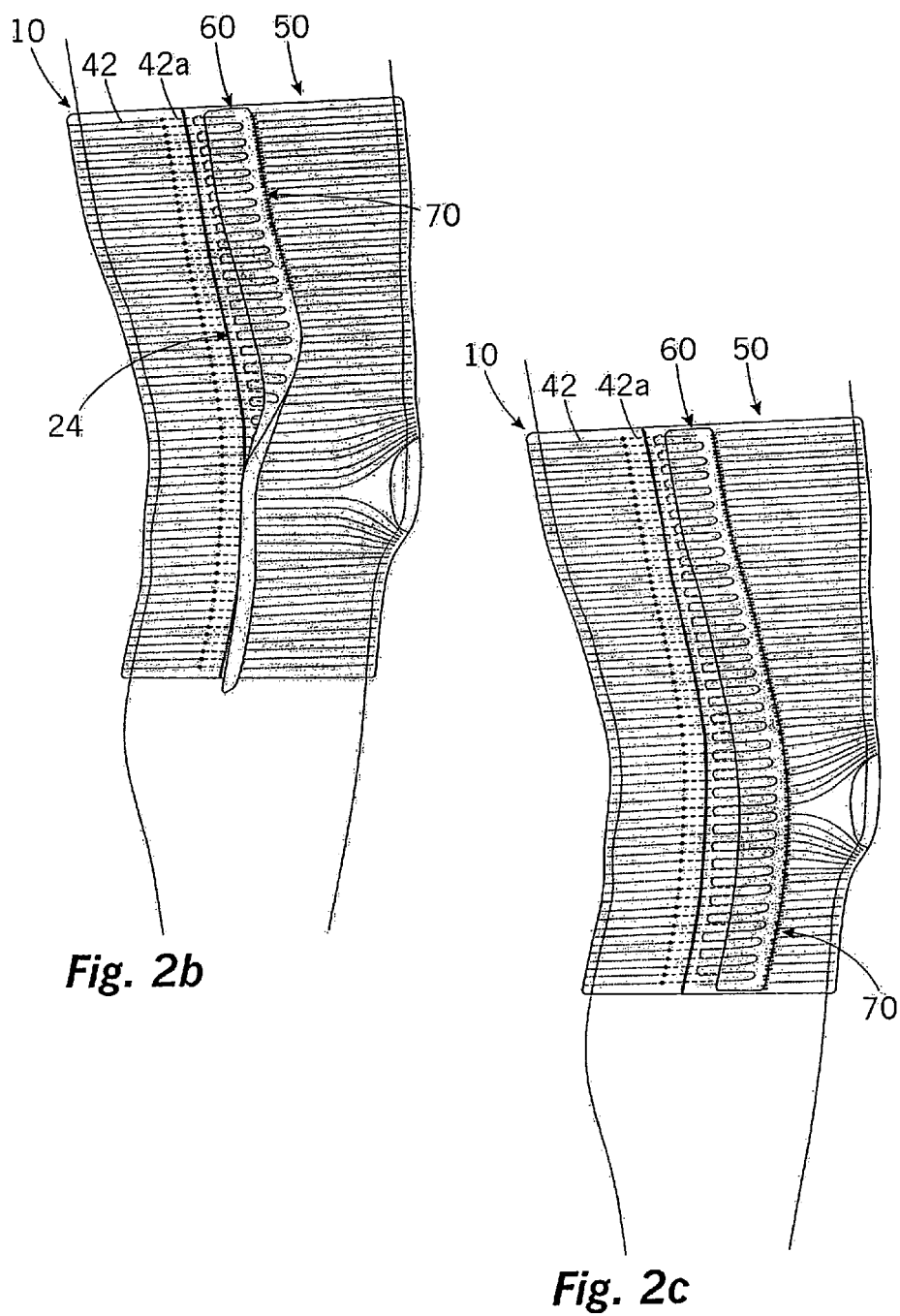

In the embodiment illustrated, however, the means of fastening is primarily implemented by means of a seam 70, as is shown in FIGS. 2b and 2c. By means of this seam 70, the handling section 60 is fastened to the outer surface of the main section 50, so that the adjustment that has previously been made in the compression threads 42 is retained. As can be seen in the illustrations of FIGS. 2b and 2c, it is in particular possible for the fastening of the handling section 60 to the main body 50 to be carried out successively, so that creation of the seam 70 can start even before the desired compressive effect has been adjusted elsewhere. As a result, skilled personnel can easily establish compressive effects suitable for each specific area.

FIG. 2 illustrates the compression bandage after the seam 70 has been completed. The compression configuration that has been established is retained even after the bandage is removed.

As soon as the success of the therapy requires an adjustment of the setting, skilled personnel can undo the seam 70, so that after modifying the length of the external portions 42a in respect of the main body 50 it can be recreated at a new place, appropriate for the changed therapeutic needs of the patient.

The seam 70 used as the means of fastening here can also be supplemented by a Velcro fastener. This makes it possible to provide preliminary fixing by means of the Velcro fastener, after which the seam 70, or some other means of fastening that cannot be changed by the patient, can provide permanent fastening—that is until the next correction is made by skilled personnel.

In the embodiment illustrated, the ability to make locally specific adjustments to the length of the external portions 42 is given by the fact that the handling section 60 is flexible in shape. Alternatively, or in addition, an arrangement with multiple handling sections can be used for the same purpose. The dotted parting line shown in FIG. 1 on the flat knitted fabric 30 indicates the possibility of separating the single handling section into two separate flat knitted fabrics 30a, 30b which will later create separate handling sections.

The embodiment as illustrated in FIGS. 2a to 2b shows the adjustment of the compression bandage when applied to the patient. This procedure is not essential. Fastening the handling section 60 to the main body 50 can also be done by skilled personnel, working on the basis of sufficient experience, when not applied to the patient.

The invention claimed is:

1. Compression bandage for surrounding a bodily member comprising:
    a piece of flexible flat material arranged to constitute a tubular member for surrounding a bodily member, where the flat material constitutes a main body that can be stretched in a circumferential direction, and
    a plurality of elastic compression threads that run in the plane of the flat material in the direction of the circumference through the flat material, and which create a compressive effect when the compression bandage is applied,
    wherein at least parts of at least some of the compression threads protrude outside the flat material forming protruding external portions allowing the compressive effect to be adjusted by varying the length of each of the protruding external portions.

2. Compression bandage according to claim 1, wherein the flat material arranged to constitute a tubular member is created by joining opposing edge regions of the flat material.

3. Compression bandage according to claim 1, wherein at least some of the compression threads are part of a common thread that passes back and forth a number of times between edge regions of the flat material.

4. Compression bandage according to claim 1, wherein exit locations at which the protruding external portions of the compression threads emerge from the flat material are located at a distance of at least 5 mm from an associated edge.

5. Compression bandage according to claim 4, wherein the exit locations at which the protruding external portions of the compression threads emerge from the flat material are located at a distance of at least 10 mm from the associated edge.

6. Compression bandage according to claim 1, wherein at least some of the protruding external portions are joined to a handling section which can be employed to pull the compression threads out of the flat material.

7. Compression bandage according to claim 6, wherein the flat material is implemented as a textile flat material with stitches which guide the compression threads, whereby the handling section is also implemented as a textile segment which is connected to the textile flat material only by the protruding external portions of the compression threads.

8. Compression bandage according to claim 6, wherein the handling section can be fixed or attached to an outer side of the main body by a fastener, whereby the fastener is implemented in such a way that the fastener cannot be released by a patient without using tools, and/or whereby the fastener comprises at least one of
    a seam,
    a riveted fastening,
    a welded fastening, and
    a glued fastening.

9. Compression bandage according to claim 1, wherein the compression bandage is designed as at least one of
    an arm bandage,
    a leg bandage, and
    a compression stocking.

10. Method for manufacture of a compression bandage according to claim 1, comprising the steps of:
    1. manufacturing the flexible flat material as flat knitted material on a knitting machine, whereby the compression threads are introduced to the flat knitted material during the knitting procedure, and whereby an external portion of at least some of the compression threads are brought out of the flexible flat material during the knitting process, and
    2. joining two opposing edges of the flat knitted material together in order to create the tubular main body.

11. Method according to claim 10, wherein the manufacturing step includes, at the same time as and in parallel with the manufacture of the flexible flat material, manufacturing a handling section implemented as flat knitted material, whereby free ends of the external portions of the compression threads are introduced into the flat knitted material of the handling section and are thereby fastened.

12. Compression bandage according to claim 1, wherein a plurality of handling sections are provided, each of which is joined to at least some of the elastic compression threads, each of the handling sections allowing individual degrees of desired compression which can be set in different partial areas of the compression bandage.

13. Compression bandage according to claim 1, wherein the piece of flexible flat material arranged to constitute a tubular member is substantially closed circumferentially along the length of the compression bandage.

* * * * *